United States Patent
Li et al.

(10) Patent No.: US 9,931,079 B2
(45) Date of Patent: Apr. 3, 2018

(54) CLAMP FOR SECURING A TERMINAL END OF A WIRE TO A SURFACE ELECTRODE

(75) Inventors: Wenjeng Li, Saint Johns, FL (US); Steven W. Bennett, Saint Augustine, FL (US); David John Little, II, Ponte Verda, FL (US); Maria Charles Vijay Stanislaus, Jacksonville, FL (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 715 days.

(21) Appl. No.: 13/343,283

(22) Filed: Jan. 4, 2012

(65) Prior Publication Data

US 2013/0172714 A1   Jul. 4, 2013

(51) Int. Cl.
*A61B 5/0492* (2006.01)
*A61B 5/00* (2006.01)
(Continued)

(52) U.S. Cl.
CPC .......... *A61B 5/6852* (2013.01); *A61B 1/2673* (2013.01); *A61B 5/0421* (2013.01); *A61B 5/04886* (2013.01); *A61B 5/6853* (2013.01); *A61B 5/6858* (2013.01); *A61B 5/6859* (2013.01); *A61M 16/04* (2013.01);
(Continued)

(58) Field of Classification Search
CPC . A61B 5/0421; A61B 5/04886; A61B 5/0492; A61B 2560/0468; A61B 2562/16; A61B 2562/225; A61B 2562/227; A61B 1/2673; A61N 1/0517

USPC ........ 600/380, 394, 546; 439/282, 345, 349, 439/355, 357, 363, 367, 368, 370, 901, 439/909, 100, 730; 138/166
See application file for complete search history.

(56) References Cited

U.S. PATENT DOCUMENTS

| | | | |
|---|---|---|---|
| 1,864,688 A | * | 6/1932 | Frank ....................... H01R 4/66 174/7 |
| 2,107,835 A | * | 2/1938 | Pierce .................. H01R 4/5083 174/7 |

(Continued)

FOREIGN PATENT DOCUMENTS

| CN | 2056003 U | 4/1990 |
|---|---|---|
| CN | 2232257 Y | 8/1996 |

(Continued)

OTHER PUBLICATIONS

Electric Motion Company, webpage "Telephony & CATV Products [Bronze Vise Type Connectors]" published Aug. 19, 2007, retreived via Wayback Machine Jun. 20, 2016.*

(Continued)

*Primary Examiner* — Lee S Cohen
*Assistant Examiner* — Erin M Cardinal
(74) *Attorney, Agent, or Firm* — Jeffrey J. Hohenshell

(57) ABSTRACT

A clamp for securing a terminal end of a wire to a surface electrode formed on a cylindrical tube includes a first semicylindrical element. A second semicylindrical element is configured to be attached to the first semicylindrical element to form a tubular clamp structure that is adapted to be clamped around the cylindrical tube. The tubular clamp structure includes an interior surface configured to securely hold a terminal end of a wire against a surface electrode formed on the cylindrical tube.

19 Claims, 7 Drawing Sheets

(51) Int. Cl.
*A61B 5/042* (2006.01)
*A61B 1/267* (2006.01)
*A61B 5/0488* (2006.01)
*A61M 16/04* (2006.01)

(52) U.S. Cl.
CPC .......... *A61B 1/267* (2013.01); *A61B 5/0492* (2013.01); *A61B 2562/225* (2013.01); *A61B 2562/227* (2013.01); *A61M 2230/60* (2013.01)

(56) References Cited

U.S. PATENT DOCUMENTS

| | | | |
|---|---|---|---|
| 2,429,585 A * | 10/1947 | Rogoff | H01R 4/20 174/84 C |
| 2,618,684 A * | 11/1952 | Bergan | H01R 4/22 174/87 |
| 2,872,505 A * | 2/1959 | Ustin | H01R 4/22 174/87 |
| 3,165,575 A * | 1/1965 | Lynch, Jr. | H01R 4/20 174/77 R |
| 3,494,364 A | 2/1970 | Peters | |
| 3,734,094 A | 5/1973 | Calinog | |
| 3,783,178 A * | 1/1974 | Philibert | F16L 25/01 174/78 |
| 3,892,455 A * | 7/1975 | Sotolongo | H01R 4/643 439/100 |
| 3,951,136 A * | 4/1976 | Wall | 600/380 |
| 4,090,518 A | 5/1978 | Elam | |
| 4,176,660 A * | 12/1979 | Mylrea et al. | 600/484 |
| 4,231,365 A | 11/1980 | Scarberry | |
| 4,304,239 A | 12/1981 | Perlin | |
| 4,349,031 A * | 9/1982 | Perlin | 600/380 |
| 4,369,794 A * | 1/1983 | Furler | 600/484 |
| 4,647,713 A * | 3/1987 | de Nijs et al. | 174/21 R |
| 4,776,808 A * | 10/1988 | Davidson | H01R 4/62 439/100 |
| 4,836,214 A | 6/1989 | Sramek | |
| 4,863,390 A * | 9/1989 | Cera | H01R 4/38 403/400 |
| 4,890,623 A | 1/1990 | Cook et al. | |
| 4,906,244 A | 3/1990 | Pinchuk et al. | |
| 4,960,133 A | 10/1990 | Hewson | |
| 4,967,759 A | 11/1990 | Teves | |
| 5,024,228 A | 6/1991 | Goldstone et al. | |
| 5,096,445 A * | 3/1992 | Lostumo | 439/865 |
| 5,125,406 A | 6/1992 | Goldstone et al. | |
| 5,135,001 A | 8/1992 | Sinofsky et al. | |
| 5,170,803 A | 12/1992 | Hewson et al. | |
| 5,286,211 A * | 2/1994 | McIntosh | H01R 4/64 24/486 |
| 5,364,281 A * | 11/1994 | Leto | H01R 4/643 403/378 |
| 5,379,765 A | 1/1995 | Kajiwara et al. | |
| 5,429,617 A | 7/1995 | Hammersmark et al. | |
| 5,464,404 A | 11/1995 | Abele et al. | |
| 5,554,176 A | 9/1996 | Maddison et al. | |
| 5,584,290 A * | 12/1996 | Brain | A61B 5/0421 128/204.22 |
| 5,672,065 A * | 9/1997 | Womack | H01R 4/5041 174/94 R |
| 5,782,744 A | 7/1998 | Money | |
| 5,782,774 A | 7/1998 | Shmulewitz | |
| 5,785,051 A | 7/1998 | Lipscher et al. | |
| 5,836,874 A | 11/1998 | Swanson et al. | |
| 5,864,093 A * | 1/1999 | Hecock | H01R 4/66 174/78 |
| 5,924,984 A | 7/1999 | Rao | |
| 5,972,026 A | 10/1999 | Laufer et al. | |
| 6,010,500 A | 1/2000 | Sherman et al. | |
| 6,032,065 A | 2/2000 | Brown | |
| 6,062,223 A | 5/2000 | Palazzo et al. | |
| 6,095,987 A | 8/2000 | Shmulewitz et al. | |
| 6,142,993 A | 11/2000 | Whayne et al. | |
| 6,148,222 A | 11/2000 | Ramsey, III | |
| 6,226,548 B1 | 5/2001 | Foley et al. | |
| 6,259,938 B1 | 7/2001 | Zarychta et al. | |
| 6,266,548 B1 | 7/2001 | Lamade et al. | |
| 6,266,549 B1 | 7/2001 | Melnikoff et al. | |
| 6,292,701 B1 | 9/2001 | Press et al. | |
| 6,334,068 B1 | 12/2001 | Hacker | |
| 6,343,233 B1 * | 1/2002 | Werner et al. | 607/119 |
| 6,357,447 B1 | 3/2002 | Swanson et al. | |
| 6,443,156 B1 | 9/2002 | Niklason et al. | |
| 6,547,788 B1 | 4/2003 | Maguire et al. | |
| 6,584,347 B1 | 6/2003 | Sinderby | |
| 6,626,841 B1 * | 9/2003 | Atlee, III | 600/528 |
| 6,626,899 B2 | 9/2003 | Houser et al. | |
| 6,735,471 B2 | 5/2004 | Hill et al. | |
| 6,869,431 B2 | 3/2005 | Maguire et al. | |
| 6,877,512 B2 | 4/2005 | Imai et al. | |
| 6,976,857 B1 * | 12/2005 | Shukla | H01R 4/46 439/100 |
| 7,008,419 B2 | 3/2006 | Shadduck | |
| 7,146,222 B2 | 12/2006 | Boling | |
| 7,153,146 B2 * | 12/2006 | Shimizu | H01R 9/0524 174/78 |
| 7,179,345 B2 | 2/2007 | Shkolnik | |
| 7,216,001 B2 | 5/2007 | Hacker et al. | |
| 7,293,562 B2 | 11/2007 | Malecki et al. | |
| 7,507,239 B2 | 3/2009 | Shadduck | |
| 7,583,991 B2 | 9/2009 | Rea | |
| 7,736,362 B2 | 6/2010 | Eberl et al. | |
| 7,794,256 B1 | 9/2010 | Sochor | |
| 7,972,308 B2 | 7/2011 | Putz | |
| 8,145,289 B2 | 3/2012 | Calabro' et al. | |
| 8,152,803 B2 | 4/2012 | Edwards et al. | |
| 8,224,422 B2 | 7/2012 | Mottola et al. | |
| 8,352,012 B2 | 1/2013 | Besio | |
| 8,467,844 B2 | 6/2013 | Rea et al. | |
| 8,634,894 B2 | 1/2014 | Rea et al. | |
| 8,688,237 B2 | 4/2014 | Stanislaus et al. | |
| 8,886,280 B2 | 11/2014 | Kartush | |
| 9,037,226 B2 | 5/2015 | Hacker et al. | |
| 9,060,744 B2 | 6/2015 | Li | |
| 9,289,141 B2 | 3/2016 | Lowery et al. | |
| 9,398,865 B2 | 7/2016 | Li | |
| 9,763,624 B2 | 9/2017 | Stanislaus et al. | |
| 2001/0018281 A1 * | 8/2001 | Royer | H01R 13/5045 439/100 |
| 2002/0016615 A1 | 2/2002 | Dev et al. | |
| 2002/0032468 A1 | 3/2002 | Hill et al. | |
| 2002/0188332 A1 | 12/2002 | Lurie et al. | |
| 2003/0018327 A1 | 1/2003 | Truckai et al. | |
| 2003/0074039 A1 | 4/2003 | Puskas | |
| 2004/0186461 A1 * | 9/2004 | DiMatteo | A61M 25/0017 604/539 |
| 2004/0230110 A1 | 11/2004 | Sinderby et al. | |
| 2005/0085111 A1 * | 4/2005 | Clark | H01R 4/60 439/100 |
| 2005/0113686 A1 | 5/2005 | Peckham | |
| 2005/0159659 A1 | 7/2005 | Sawan et al. | |
| 2005/0222656 A1 | 10/2005 | Wahlstrand et al. | |
| 2005/0255727 A1 * | 11/2005 | Alladice | H01R 4/66 439/100 |
| 2006/0012671 A1 | 1/2006 | Nimri et al. | |
| 2006/0025702 A1 | 2/2006 | Sterrantino et al. | |
| 2006/0116564 A1 | 6/2006 | Mintchev et al. | |
| 2006/0241725 A1 | 10/2006 | Libbus et al. | |
| 2006/0254595 A1 * | 11/2006 | Rea | 128/207.14 |
| 2007/0074728 A1 * | 4/2007 | Rea | 128/207.14 |
| 2007/0137651 A1 | 6/2007 | Glassenberg et al. | |
| 2007/0142888 A1 | 6/2007 | Chavez | |
| 2007/0156041 A1 | 7/2007 | Rea | |
| 2007/0170928 A1 | 7/2007 | Fedan et al. | |
| 2007/0219551 A1 | 9/2007 | Honour et al. | |
| 2008/0077043 A1 | 3/2008 | Malbrain et al. | |
| 2008/0140052 A1 | 6/2008 | Moller et al. | |
| 2008/0177190 A1 | 7/2008 | Libbus et al. | |
| 2008/0249507 A1 | 10/2008 | Hadani | |
| 2008/0255441 A1 * | 10/2008 | Hadani | A61B 1/00105 600/373 |
| 2008/0300650 A1 | 12/2008 | Gerber et al. | |
| 2009/0227885 A1 | 9/2009 | Lowery et al. | 600/526 |

(56) References Cited

U.S. PATENT DOCUMENTS

| | | | |
|---|---|---|---|
| 2010/0006103 A1 | 1/2010 | McGinnis et al. | |
| 2010/0036229 A1 | 2/2010 | Weekamp et al. | |
| 2010/0063376 A1 | 3/2010 | Kartush | |
| 2010/0087782 A1 | 4/2010 | Ghaffari et al. | |
| 2010/0145178 A1 | 6/2010 | Kartush | |
| 2010/0168561 A1 | 7/2010 | Anderson | |
| 2010/0168743 A1 | 7/2010 | Stone et al. | |
| 2010/0179417 A1 | 7/2010 | Russo | |
| 2010/0191311 A1 | 7/2010 | Scheiner et al. | |
| 2010/0198099 A1 | 8/2010 | Murphy et al. | |
| 2010/0317956 A1 | 12/2010 | Kartush | |
| 2011/0023889 A1 | 2/2011 | Lin et al. | |
| 2011/0030694 A1 | 2/2011 | Schaner et al. | |
| 2011/0071379 A1* | 3/2011 | Rea et al. | 600/373 |
| 2011/0190596 A1 | 8/2011 | Hacker et al. | |
| 2011/0230734 A1 | 9/2011 | Fain et al. | |
| 2011/0245647 A1 | 10/2011 | Stanislaus et al. | |
| 2011/0301587 A1 | 12/2011 | Deem et al. | |
| 2011/0306861 A1* | 12/2011 | Thramann et al. | 600/373 |
| 2012/0016256 A1 | 1/2012 | Mabary et al. | |
| 2012/0024292 A1 | 2/2012 | Sandmore et al. | |
| 2012/0055257 A1 | 3/2012 | Shaw-Klein | |
| 2014/0148672 A1 | 5/2014 | Li | |
| 2014/0155720 A1 | 6/2014 | Stanislaus et al. | |
| 2014/0275914 A1 | 9/2014 | Li et al. | |
| 2015/0250423 A1 | 9/2015 | Hacker et al. | |
| 2016/0038072 A1 | 2/2016 | Brown et al. | |
| 2016/0038073 A1 | 2/2016 | Brown et al. | |
| 2016/0038074 A1 | 2/2016 | Brown et al. | |
| 2016/0262699 A1 | 9/2016 | Goldstone et al. | |
| 2016/0287112 A1 | 10/2016 | McFarlin et al. | |
| 2016/0287861 A1 | 10/2016 | McFarlin et al. | |
| 2016/0324475 A1 | 11/2016 | Hacker | |
| 2016/0345905 A1 | 12/2016 | Li | |
| 2017/0007146 A1 | 1/2017 | Schulhauser et al. | |

FOREIGN PATENT DOCUMENTS

| | | | |
|---|---|---|---|
| CN | 2827273 Y | | 10/2006 |
| DE | 29715344 U1 | | 2/1998 |
| DE | 19750705 C1 | | 3/2000 |
| EP | 0438863 A1 | | 11/1990 |
| EP | 1750368 A1 | | 2/2007 |
| GB | 1214718 A | | 12/1970 |
| JP | H03-182230 | | 8/1991 |
| JP | 2001224554 A | | 8/2001 |
| JP | 2003-019200 | | 1/2003 |
| JP | 2003-527164 | | 9/2003 |
| JP | 2006-528890 | | 12/2006 |
| JP | 2007-532152 | | 11/2007 |
| JP | 2007307185 A | | 11/2007 |
| JP | 2009519763 A | | 5/2009 |
| JP | 2009-524482 | | 7/2009 |
| WO | 9723163 A1 | | 7/1997 |
| WO | 01/41638 A1 | | 6/2001 |
| WO | 2004/100786 A1 | | 11/2004 |
| WO | 2005/097246 A1 | | 10/2005 |
| WO | 2006012671 A1 | | 2/2006 |
| WO | 2006012672 A1 | | 2/2006 |
| WO | 2007078827 A2 | | 7/2007 |
| WO | 2007/089491 A2 | | 8/2007 |
| WO | 2008091928 A2 | | 7/2008 |
| WO | 2011041690 A1 | | 4/2011 |
| WO | 2013008106 A1 | | 1/2013 |

OTHER PUBLICATIONS

Southern Grounding Products, webpage "Grounding & Ground Rod Clamps" published Nov. 19, 2008, retreived via Wayback Machine Jun. 20, 2016.*
Non-Final Office Action for U.S. Appl. No. 12/896,578 dated Oct. 3, 2012, 16 pgs.
Non-Final Office Action for U.S. Appl. No. 12/896,593, dated Sep. 5, 2012, 19 pgs.
Final Office Action for U.S. Appl. No. 12/896,593, dated Jan. 3, 2013, 13 pgs.
PCT Search Report dated Feb. 4, 2011 for PCT/US2010/051145 (15 pgs.).
PCT Search Report dated Apr. 28, 2011 for PCT/US2010/051132 (17 pgs.).
International Preliminary Report on Patentability dated Oct. 24, 2011 for PCT/US2010/051145 (12 pgs.).
Non-Final Office Action dated Sep. 19, 2013 in U.S. Appl. No. 12/896,578, 12 pgs.
International Preliminary Report on Patentability for PCT/US10/51132, dated Dec. 5, 2011, 5 pgs.
Japanese Office Action for Application No. 2012-532355, dated Apr. 18, 2014, 7 pgs.
Australian Examination Report for Application No. 2010300379, dated May 30, 2014, 4 pgs.
Japanese Office Action for Application No. 2012-532356, dated Apr. 18, 2014, 7 pgs.
European Examination Report for Application No. 10781544.1, dated Feb. 19, 2014, 4 pgs.
European Examination Report for Application No. 10779358.0, dated Feb. 19, 2014, 4 pgs.
Chinese Office Action for Application No. 201080054559.2, dated Jul. 17, 2014, 10 pgs.
Chinese Office Action for Application No. 201080054850.X, dated Jul. 23, 2014, 6 pgs.
Australian Examination Report dated Feb. 25, 2013, 4 pgs.
Chinese Office Action dated Feb. 14, 2014, 5 pgs.
Chinese Office Action dated Feb. 20, 2014, 19 pgs.
Non-Final Office Action for U.S. Appl. No. 14/175,165, dated Mar. 3, 2015, 12 pgs.
Non-Final Office Action for U.S. Appl. No. 14/175,165, dated Aug. 15, 2014, 17 pgs.
Final Office Action for U.S. Appl. No. 14/175,165, dated Dec. 4, 2014, 13 pgs.
Extended European Search Report for Appl. No. 14182496.1, dated Nov. 28, 2014, 7 pgs.
Advisory Action for U.S. Appl. No. 12/896,593 dated Apr. 10, 2013 (7 pages).
Notice of Allowance for U.S. Appl. No. 12/896,593 dated Aug. 15, 2013 (11 pages).
Notice of Allowance for U.S. Appl. No. 12/896,593 dated Nov. 7, 2013 (13 pages).
Notice of Allowance for U.S. Appl. No. 14/175,165 dated May 29, 2014 (28 pages).
Final Office Action for U.S. Appl. No. 14/175,165, dated Jun. 12, 2015 (16 pages).
Advisory Action for U.S. Appl. No. 14/175,165, dated Sep. 25, 2015 (6 pages).
Final Office Action for U.S. Appl. No. 14/175,165, dated Jun. 12, 2015, 16 pgs.
Non-Final Office Action for U.S. Appl. No. 14/175,165 dated Jan. 5, 2016 (22 pages).
International Search Report and Written Opinion, PCT/US2014/027810, dated Jul. 25, 2014 (18 pages).
"Applications of High-Pressure Balloons in the Medical Device Industry", 1999 Advanced Polymers, Inc. 1999, Mark A. Saab, President (19 pages).
International Search Report and Written Opinion, PCT/US2013/072193, dated Mar. 11, 2014 (18 pages).
Defendants' Invalidity Contentions and Document Production Pursuant to Patent Local Rules 3-3 and 3-4; *Neurovision Medical Products, Inc.* v. *Medtronic Public Limited Company, Medtronic, Inc.; Medtronic Xomed, Inc. HCA Holdings, Inc.; and Healthtrust Purchasing Group, L.P.*; Civ. No. 2:16-cv-00127-JRP-RSP, signed by James M. Hilmert, date Jun. 10, 2016 (147 pages).
Hon, Li & Hutchings, "Direct writing technology—Advances and developments," CIRP Annals—Manufacturing Technology, vol. 57, Issue 2, presented on Aug. 25, 2008 and published Oct. 28, 2008, pp. 601-620 (20 pages).

(56) References Cited

OTHER PUBLICATIONS

Kartush et al., "Intraoperative Facial Nerve Monitoring," Ch. 5, Neuromonitoring in Otology and Head and Neck Surgery, Raven Press, Ltd., p. 99-120 (1992) (22 pages).
Goldstone A., Schettino R., "The Electrode Endotracheal Tube: A State of the Art Method for Monitoring the Recurrent Laryngeal Nerve-Vocal Cord Muscle Integrity in the Intubated Patient," presented to the American Academy of Otolaryngology/Head & Neck Surgery Annual National Meeting, San Diego, CA. (Sep. 1990) (1 page).
Eisle D.W., Goldstone A., "Electrophysiologic Identification and Preservation of the Superior Laryngeal Nerve During Thyroid Surgery," The Laryngescope, vol. 101, Issue 3, pp. 313-315 (Mar. 1991) (3 pages).
Bakhshaee et al., "Evaluation of the Distance Between Anterior Commissure of True Vocal Folds and the First Tracheal Ring and Related Laryngeal Indices in 40 Human Cadavers," J. Voice, vol. 30, No. 2, p. 159, col. 1 (2016) (3 pages).
Sprinzl et al., "Morphometric Measurements of the Cartilaginous Larynx: an Anatomic Correlate of Laryngeal Surgery," Head & Neck, Figs. 3-4, Tables 2-3, p. 743-750 (Dec. 1999) (8 pages).
Witt, Robert L., "Recurrent Laryngeal Nerve Electrophysiologic Monitoring in Thyroid Surgery: The Standard of Care?" J. Voice, vol. 19, No. 3, pp. 497-500 (2005) (4 pages).
Strauss, Christian et al., "Electrophysiological Localization of Motor Areas within the Rhomboid Fossa During Brainstem Surgery," ECoG, OAE and Intraoperative Monitoring: Proceedings of the First International Conference, (D. Hohmann, ed.) pp. 375-378 (Sep. 1992) (10 pages).
Møller, Aage R., "Monitoring and Mapping the Cranial Nerves and the Brainstem," Ch. 13, Neurophysiology in Nuerosurgery: A Modern Intraoperative Approach, Academic Press, pp. 291-318 (2002) (36 pages).
Nang et al., "Prognostic Indicators of Unilateral Vocal Fold Paralysis," Archives of Otolaryngology Head Neck Surgery, vol. 134, No. 4, pp. 380-388 (Apr. 2008) (11 pages).
Dimopoulos et al., "Quantitative Estimation of the Recurrent Laryngeal Nerve Irritation by Employing Spontaneous Intraoperative Electromyographic Monitoring During Anterior Cervical Discectomy and Fusion," J. Spinal Disorder Tech, vol. 22, No. 1, pp. 1-7 (Feb. 2009) (7 pages).
Ajmani, M. L., "A Metrical Study of the Laryngeal Skeleton in Adult Nigerians," J. Anat., vol. 171, pp. 187-191 (1990) ("Ajmani Article") (5 pages).
Grillo, Hermes, Surgery of the Trachea and Bronchi, BC Decker Inc., pp. 39-59 (2004) (23 pages).
Livingstone, Churchill, Gray's Anatomy, pp. 1637-1657 (1995) (28 pages).
Special 510(k) Premarket Notification, K094054, Neurovision® EMG Endotracheal Tube dated May 14, 2010 (6 pages).
Pictures of a NuVasive EMG tube (5 pages). The first public use of the NuVasive EMG tube is unclear to Applicant. For purposes of Examination only, the NuVasive EMG tube may be considered to be prior art to the present application, although Applicant reserves the right to challenge this in any future proceeding. Applicant also intends to submit a physical sample of the NuVasive EMG tube in U.S. Appl. No. 15/217,572, filed Jul. 22, 2016.
U.S. Appl. No. 13/688,818, Notice of Allowance dated Feb. 20, 2015 (7 pages).
U.S. Appl. No. 13/688,818, Final Office Action dated Jun. 25, 2014 (10 pages).
U.S. Appl. No. 13/688,818, Non-Final Office Action dated Mar. 13, 2014 (10 pages).
U.S. Appl. No. 14/747,257, Non-Final Office Action dated Nov. 17, 2015 (10 pages).
U.S. Appl. No. 14/747,257, Notice of Allowance dated Mar. 23, 2016 (5 pages).
U.S. Appl. No. 13/826,323, Examiner's Answer dated Nov. 18, 2015 (6 pages).
U.S. Appl. No. 13/826,323, Advisory Action dated May 28, 2015 (3 pages).
U.S. Appl. No. 13/826,323, Final Office Action dated Mar. 23, 2015 (6 pages).
U.S. Appl. No. 13/826,323, Non-Final Office Action dated Dec. 15, 2014 (11 pages).
U.S. Appl. No. 13/826,323, Non-Final Office Action dated Sep. 8, 2014 (9 pages).
David L. Bourell et al., Solid Freeform Fabrication Proceedings, Aug. 2004, © 2004 The University of Texas at Austin (15 pages).
ECOM™ Brochure for Endotracheal Cardiac Output Monitor, © 2008 ConMed Corporation Sep. 2008 (2 pages).
James K. Brown et al., Parasympathetic Innervation of the Cervical Trachealis Muscle in Living Dogs, © 1982 The American Physiology Society, vol. 53, No. 3, pp. 617-625 (9 pages).
NuVasive® NVJBB® EMG Endotracheal Tube IFU Product Insert (2 pages).
NuVasive® NeuroVision® EMG Endotracheal Tube brochure—© 2010 NuVasive, Inc. (4 pages).
Cahide Topsakal et al., Intraoperative Monitoring of Lower Cranial Nerves in Skull Base Surgery: Technical Report and Review of 123 Monitored Cases, Neurosurg. Rev., vol. 31, pp. 45-52 Published Online Oct. 24, 2007 © Springer-Verlag 2007 (9 pages).
Jasper R. Daube et al., Clinical Neurophysiology, Third Edition, Oxford University Press. Chapters 25, 43 and 44, © 2009 (71 pages).
U.S. Appl. No. 15/217,572, filed Jul. 22, 2016, Inventor: David C. Hacker (65 pages).
U.S. Appl. No. 61/244,402, filed Sep. 21, 2009 (5 pages).
Non-Final Office Action for U.S. Appl. No. 15/219,726 dated Apr. 11, 2017 (23 pages).
Decision; *Medtronic Xomed, Inc.* v. *Neurovision Medical Products, Inc.*; PTAB Case IPR2016-01847; for U.S. Pat. No. 8,467,844 entered Mar. 23, 2017 (37 pages).
Restriction Requirement for U.S. Appl. No. 12/896,578 dated Jul. 24, 2012 (8 pages).
Notice of Allowance for U.S. Appl. No. 12/896,578 dated Feb. 27, 2014 (7 pages).
Notice of Allowance for U.S. Appl. No. 12/896,578 dated Jun. 9, 2014 (11 pages).
Notice of Allowance for U.S. Appl. No. 12/896,578 dated Aug. 5, 2014 (12 pages).
Notice of Allowance for U.S. Appl. No. 12/896,578 dated Oct. 6, 2014 (11 pages).
Notice of Allowance for U.S. Appl. No. 12/896,578 dated Jan. 28, 2015 (12 pages).
Notice of Allowance for U.S. Appl. No. 12/896,578 dated Mar. 30, 2015 (11 pages).
Canadian 1st Examiner's Report for 2775588 dated Oct. 28, 2016 (4 pages).
Restriction Requirement for U.S. Appl. No. 14/716,351 dated Jan. 22, 2016 (5 pages).
Non-Final Office Action for U.S. Appl. No. 14/716,351 dated May 3, 2016 (25 pages).
Non-Final Office Action for U.S. Appl. No. 14/716,351 dated Sep. 21, 2016 (6 pages).
Australian Examination Report No. 1 for Application No. 2015200049, dated Mar. 10, 2016 (3 pages).
Canadian 1st Examiner's Report for 2776163 dated Oct. 28, 2016 (4 pages).
Extended European Search Report for Application No. 16176750.4, dated Nov. 22, 2016 (6 pages).
Japanese Office Action for Application No. 2014/189873, dated Aug. 30, 2015 (5 pages).
Final Office Action for U.S. Appl. No. 14/175,165 dated May 19, 2016 (24 pages).
Australian 1st Examination Report for 2012363699 dated Sep. 8, 2016 (3 pages).
Chinese 1st Office Action for 201280071074.3 dated Oct. 30, 2015 (12 pages).
Japanese 1st Office Action for 2014-551252 dated Oct. 20, 2016 (3 pages).

(56) References Cited

OTHER PUBLICATIONS

Non-Final Office Action for U.S. Appl. No. 13/688,818 dated Oct. 9, 2014 (7 pages).
Australian 1st Examination Report for 2013406220 dated May 19, 2016 (3 pages).
Final Office Action mailed for U.S. Appl. No. 15/219,726 dated Oct. 21, 2016 (34 pages).
Advisory Action for U.S. Appl. No. 15/219,726 dated Jan. 5, 2017 (4 pages).
European Office Action for Application No. 14720826.8, dated Aug. 2, 2016 (8 pages).
U.S. Appl. No. 14/945,167, filed Nov. 18, 2015 (89 pages).
U.S. Appl. No. 14/945,208, filed Nov. 18, 2015 (88 pages).
Non-Final Office Action for U.S. Appl. No. 15/217,572 dated Feb. 9, 2017 (13 pages).
Affidavit of Christopher Butler with Exhibit A dated Nov. 10, 2016 (8 pages).
Decision-Institution of Inter Partes Review; *Medtronic Xomed, Inc.* v. *Neurovision Medical Products, Inc.*; PTAB Case IPR2016-01405; for U.S. Pat. No. 8,634,894 entered Dec. 29, 2016 (35 pages).
Petition for Inter Partes Review; *Medtronic Xomed, Inc.* v. *Neurovision Medical Products, Inc.*; PTAB Case IPR2017-00456; for U.S. Pat. No. 8,634,894 dated Dec. 9, 2016 (58 pages).
Patentee's Preliminary Response to Petition for Inter Partes Review; *Medtronic Xomed, Inc.* v. *Neurovision Medical Products, Inc.*; PTAB Case IPR2016-01405; for Patent No. 8,634,894 dated Oct. 20, 2016 (74 pages).
Declaration of Mike Lieu—Exhibit 2002 to Patentee's Preliminary Response to Petition for Inter Partes Review dated Oct. 20, 2016 (7 pages).
Declaration of Stephen W. Blakely—Exhibit 2003 to Patentee's Preliminary Response to Petition for Inter Partes Review dated Oct. 20, 2016 (7 pages).
Declaration of James Lee Rea—Exhibit 2004 to Patentee's Preliminary Response to Petition for Inter Partes Review dated Oct. 20, 2016 (6 pages).
Declaration of Ryan M. Rea—Exhibit 2005 to Patentee's Preliminary Response to Petition for Inter Partes Review dated Oct. 20, 2016 (2 pages).
"Thyroid Surgery May Result in Paralysis of Vocal Cords," Wall Street Journal article dated Aug. 10, 2001 to Exhibit 2006 to Patentee's Preliminary Response to Petition for Inter Partes Review dated Oct. 20, 2016 (4 pages).
Medtronic webpage at http://medtronic.com/us-en/healthcare-nim-nerve-monitoring-systems/related-nerve-monitoring-products.html—Exhibit 2007 to Patentee's Preliminary Response to Petition for Inter Partes Review dated Oct. 20, 2016 (5 pages).
Medtronic product recall notice—Exhibit 2008 to Patentee's Preliminary Response to Petition for Inter Partes Review dated Oct. 20, 2016 (4 pages).
MicroPenning: How It Works—Exhibit 2009 to Patentee's Preliminary Response to Petition for Inter Partes Review dated Oct. 20, 2016 (2 pages).
MicroPenning: Overview—Exhibit 2010 to Patentee's Preliminary Response to Petition for Inter Partes Review dated Oct. 20, 2016 (3 pages).
U.S. Pat. No. 4,461,304 to Kuperstein—Exhibit 2011 to Patentee's Preliminary Response to Petition for Inter Partes Review dated Oct. 20, 2016 (10 pages).
Provisional U.S. Appl. No. 61/126,567—Exhibit 2012 to Patentee's Preliminary Response to Petition for Inter Partes Review dated Oct. 20, 2016 (8 pages).
NuVasive, Inc.'s Petition for Inter Partes Review file in IPR2015-00502—Exhibit 2014 to Patentee's Preliminary Response to Petition for Inter Partes Review dated Oct. 20, 2016 (63 pages).
PTAB's Decision dated Jul. 16, 2015 in IPR2015-00502—Exhibit 2015 to Patentee's Preliminary Response to Petition for Inter Partes Review dated Oct. 20, 2016 (31 pages).
Table of page cites and summary regarding Exhibit 2001—Exhibit 2016 to Patentee's Preliminary Response to Petition for Inter Partes Review dated Oct. 20, 2016 (14 pages).
Redacted Exhibit 2001— Confidential Neurovision emails regarding conception and reduction to practice—Exhibit 2017 to Patentee's Preliminary Response to Petition for Inter Partes Review dated Oct. 20, 2016 (140 pages).
Notice of Allowance for U.S. Appl. No. 14/175,165 dated Feb. 23, 2017 (13 pages).
Korean 1st Office Action for 10-2012-7011251 dated Feb. 6, 2017 (13 pages).
Corrected Notice of Allowability for U.S. Appl. No. 14/175,165 dated Mar. 23, 2017 (18 pages).
Final Office Action for U.S. Appl. No. 14/716,351 dated Mar. 21, 2017 (30 pages).
Non-Final Office Action for U.S. Appl No. 14/716,351 dated May 17, 2017 (13 pages).
Notice of Allowance for U.S. Appl. No. 14/175,165 dated May 22, 2017 (12 pages).
Final Office Action for U.S. Appl. No. 15/217,572 dated Jun. 6, 2017 (22 pages).
Notice of Allowance for U.S. Appl. No. 13/826,323 dated Jun. 7, 2017 (5 pages).
European Office Action for Application No. 14720826.8, dated Feb. 1, 2017 (6 pgs).
Korean Final Office Action for 10-2012-7011251 dated Jun. 28, 2017 (7 pages).
Australian 2nd Examination Report for 2012363699 dated Jun. 22, 2017 (6 pages).
Australian 1st Examination Report for Application No. 2014236572, dated Aug. 10, 2017 (4 pgs).
Japanese 1st Office Action for 2016-502632 dated Jul. 7, 2017 (8 pages).
Final Office Action for U.S. Appl. No. 15/219,726 dated Aug. 2, 2017 (10 pages).
Canadian 2nd Examiner's Report for 2775588 dated Sep. 5, 2017 (4 pages).
Australian 3nd Examination Report for 2012363699 dated Sep. 5, 2017 (3 pages).
Notice of Allowance for U.S. Appl. No. 13/826,323 dated Sep. 12, 2017 (45 pages).
Notice of Allowance for U.S. Appl. No. 14/716,351 dated Sep. 27, 2017 (11 pages).
Advisory Action for U.S. Appl. No. 15/217,572 dated Sep. 29, 2017 (4 pages).
Notice of Allowance for U.S. Appl. No. 15/217,572 dated Nov. 3, 2017 (10 pages).
International Search Report and Written Opinion, PCT/US2012/069253, dated Feb. 28, 2013 (8 pages).
European Examination Report for Application No. 12818693.9 dated Oct. 25, 2017 (7 pages).
European Office Action for Application No. 13812262.7, dated Aug. 2, 2017 (8 pages).
Notice of Allowance for U.S. Appl. No. 15/219,726 dated Oct. 2, 2017 (8 pages).
European Office Action for Application No. 14720826.8, dated Jul. 17, 2017 (6 pgs).

* cited by examiner

CLAMP FOR SECURING A TERMINAL END OF A WIRE TO A SURFACE ELECTRODE

BACKGROUND

Endotracheal tubes include electrodes that are designed to make contact with a patient's vocal cords to facilitate electromyographic (EMG) monitoring of the vocal cords during surgery when connected to an EMG monitoring device. Endotracheal tubes provide an open airway for patient ventilation, and provide for monitoring of EMG activity of the intrinsic laryngeal musculature when connected to an appropriate EMG monitor. Endotracheal tubes can provide continuous monitoring of the nerves supplying the laryngeal musculature during surgical procedures.

In endotracheal tubes, wires are typically terminated to surface electrodes on the tube. Terminating wires to surface electrodes for endotracheal tubes usually involves the use of a flex circuit and electrically conductive epoxy. However, flex circuits are expensive, and conductive epoxy can be messy and cause short circuits.

SUMMARY

One embodiment is directed to a clamp for securing a terminal end of a wire to a surface electrode formed on a cylindrical tube. The clamp includes a first semicylindrical element. A second semicylindrical element is configured to be attached to the first semicylindrical element to form a tubular clamp structure that is adapted to be clamped around the cylindrical tube. The tubular clamp structure includes an interior surface configured to securely hold a terminal end of a wire against a surface electrode formed on the cylindrical tube.

DETAILED DESCRIPTION

Figure 1:
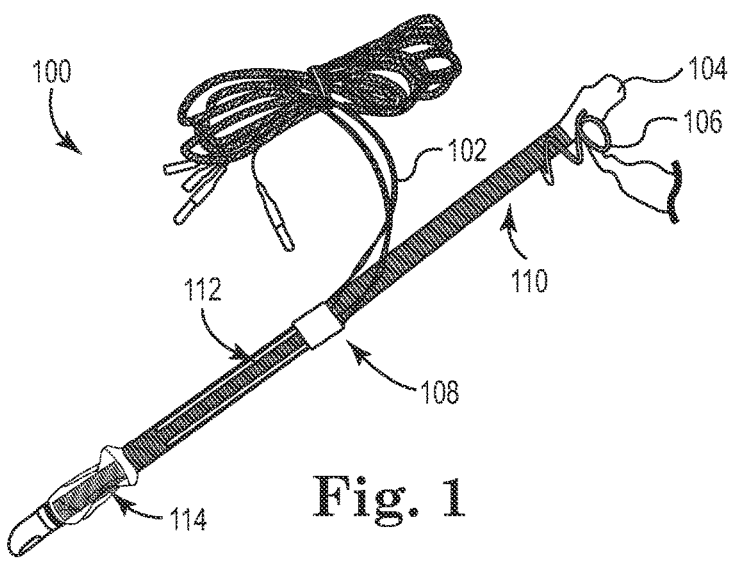
FIG. 1 is a diagram illustrating an EMG endotracheal tube with conductive ink electrodes printed on the tube according to one embodiment.
Figure 2:
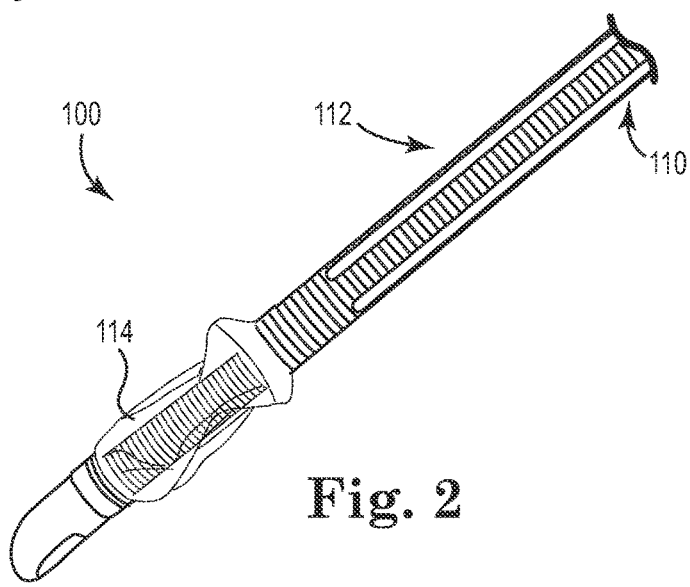
FIG. 2 is a diagram illustrating a close-up view of a portion of the endotracheal tube shown in FIG. 1 according to one embodiment.

FIG. 1 is a diagram illustrating an EMG endotracheal tube 100 with conductive ink electrodes printed on the tube according to one embodiment. FIG. 2 is a diagram illustrating a close-up view of a portion of the endotracheal tube 100 shown in FIG. 1 according to one embodiment. Endotracheal tube 100 includes solid wires 102, fitting 104, cuff inflating conduit 106, plastic (e.g., PVC) tube 110, conductive ink electrodes 112, and primary cuff 114. Solid wires 102 are connected to conductive ink electrodes 112 by interconnection structure 108. Tube 110 transports gases to and from the lungs. Fitting 104 is configured to be connected to a respirating machine (not shown) for injecting air into the lungs and withdrawing air from the lungs. Cuff inflating conduit 106 is configured to be connected to a source of compressed air (not shown) for inflating cuff 114. Cuff inflating conduit 106 communicates with a lumen 122 (FIG. 3) located in the wall 120 of tube 110, and the lumen 122 communicates with primary cuff 114. After endotracheal tube 100 is inserted into the trachea of a patient, conductive ink electrodes 112 sense EMG signals, which are output to an EMG processing machine via solid wires 102.

Figure 3:
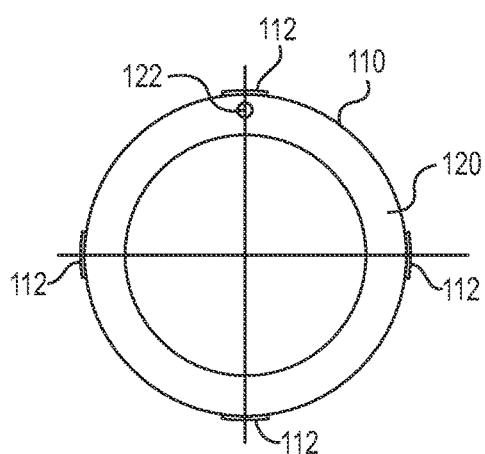
FIG. 3 is a diagram illustrating a cross-sectional view of the endotracheal tube shown in FIG. 1 according to one embodiment.

FIG. 3 is a diagram illustrating a cross-sectional view of the endotracheal tube 100 shown in FIG. 1 according to one embodiment. As shown in FIG. 3, lumen 122 is located in the wall 120 of tube 110 for inflating the cuff 114. Conductive ink electrodes 112 are formed on the exterior surface of wall 120. In one embodiment, conductive ink electrodes 112 are formed by tracing or printing a silver filled polymer conductive ink or a carbon conductive ink on tube 110. Conductive inks are available in variety of flowable material choices such as Silver, Carbon, Gold, Platinum, Palladium, Silver-Tungsten, and Silver-Titanium. Conductive inks can be deposited on the substrate using various known technologies such as PAD printing, Screen printing, Ink jet dispensing, digital printing, Micropen dispensing, painting, vapor deposition, and plasma sputtering. Conductive inks can be used both for stimulation and recording purposes in nerve monitoring applications.

Terminating wires, such as wires 102, to surface electrodes, such as electrodes 112, usually involves use of a flex circuit and electrically conductive epoxy. However, flex circuits are expensive, and conductive epoxy can be messy and cause short circuits. In one embodiment, a solderless interference fit clamp is used for interconnection structure 108, and the terminal ends of the wires 102 are sandwiched between the interior surface of the clamp 108 and the electrodes 112 formed on the tube 110. The clamp 108 securely holds the terminal ends of the wires 102 against the electrodes 112 without the use of a flex circuit, conductive epoxy, or soldering.

Figure 4:
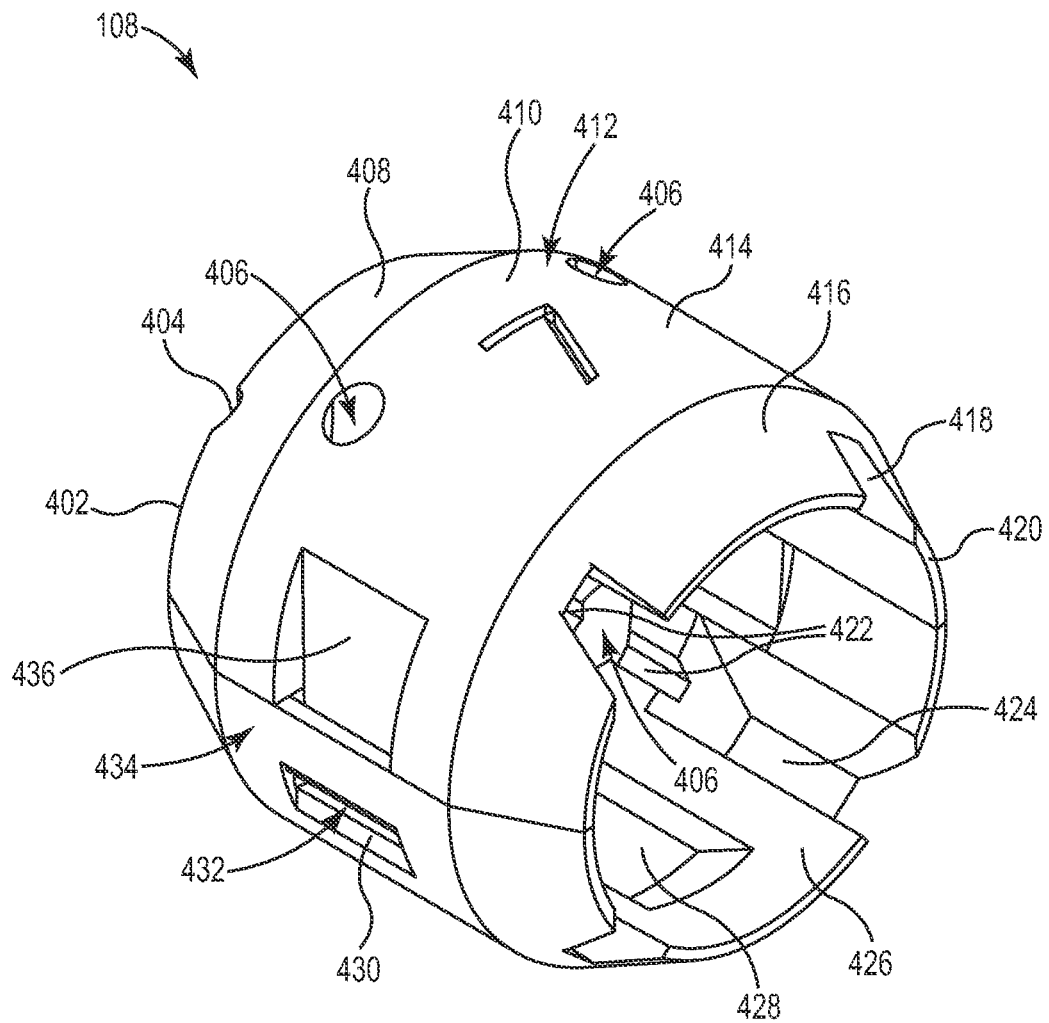
FIG. 4 is a diagram illustrating a perspective view of an interconnection structure according to one embodiment.

FIG. 4 is a diagram illustrating a perspective view of an interconnection structure 108 according to one embodiment. In the illustrated embodiment, interconnection structure 108 is a tubular clamp structure that clamps around the tube 110 and secures a terminal end of each one of the solid wires 102 to a respective one of the conductive ink electrodes 112. Interconnection structure 108 includes a semicylindrical male element 412 and a semicylindrical female element 434, which are connected together to form the tubular clamp structure 108. Clamp structure 108 has a distal end 402 and a proximal end 420. Clamp structure 108 includes a tapered distal end portion 408, a tapered proximal end portion 416, and a cylindrical central portion 410 positioned between the two end portions 408 and 416. The two tapered end portions 408 and 416 are configured to form a friction fit or compression fit against the tube 110, and thereby prevent the structure 108 from sliding along the tube 110.

Male element 412 includes two flexible clips 436, and female element 434 includes two openings 432. Each of the clips 436 includes a protrusion 430 that is configured to be inserted into a respective one of the openings 432 in the female element 434, and thereby hold the male element 412 and the female element 434 together.

Four notches 404 are formed in the distal end 402 of the clamp 108 (two notches 404 in the male element 412 and two notches 404 in the female element 434). In one embodiment, the four notches 404 are substantially evenly spaced apart around a circular periphery of the distal end 402, and are configured to be longitudinally aligned with four respective ones of the electrodes 112 on the tube 110. The notches 404 provide clearance space for the electrodes 112 so that the distal end 402 of the clamp 108 contacts the tube 110 in the regions between notches 404, but does not contact the tube 110 at the locations of the notches 404, and does not contact the electrodes 112.

Four notches 418 are formed in the proximal end 420 of the clamp 108 (two notches 418 in the male element 412 and two notches 418 in the female element 434). In one embodiment, the four notches 418 are substantially evenly spaced apart around a circular periphery of the proximal end 420, and are configured to be longitudinally aligned with four respective ones of the electrodes 112 on the tube 110. The notches 418 provide clearance space for the solid wires 102 so that the proximal end 420 of the clamp 108 contacts the tube 110 in the regions between notches 418, but does not contact the tube 110 at the locations of the notches 418, and does not pinch the solid wires 102 against the tube 110.

Four circular holes 406 are formed in the central portion 410 of the clamp 108 (two holes 406 in the male element 412 and two holes 406 in the female element 434), and extend from an exterior surface 414 of the clamp 108 to an interior surface 426 of the clamp 108. In one embodiment, the four holes 406 are substantially evenly spaced apart around a circumference of the central portion 410, and are longitudinally aligned with respective ones of the notches 404 and 418.

Two rectangular-shaped cavities 428 are formed in the interior surface 426 of the central portion 410 (one cavity 428 in the male element 412 and one cavity 428 in the female element 434). The two cavities 428 face each other on the interior surface 426 (i.e., the cavities are spaced apart by about 180 degrees around a circumference of the interior surface 426).

Four longitudinal shallow trenches 422 and four longitudinal deep trenches 424 are formed in the interior surface 426 of the clamp 108 (two shallow trenches 422 in the male element 412 and two shallow trenches 422 in the female element 434, and two deep trenches 424 in the male element 412 and two deep trenches 424 in the female element 434). Respective ones of the shallow trenches 422 and the deep trenches 424 are longitudinally aligned with each other, and longitudinally aligned with respective ones of the notches 404 and 418 and holes 406. Thus, clamp 108 includes four sets of a longitudinally aligned notch 404, hole 406, notch 418, shallow trench 422, and deep trench 424. In one embodiment, the four shallow trenches 422 and the four deep trenches 424 are substantially evenly spaced apart around a circumference of the interior surface 426. Each of the shallow trenches 422 longitudinally extends proximally and distally from a respective one of the holes 406. Each of the shallow trenches 422 longitudinally extends from a distal end of a respective one of the deep trenches 424 to a respective one of the notches 404 in the distal end 402. Each of the deep trenches 424 longitudinally extends from a proximal end of a respective one of the shallow trenches 422 to a respective one of the notches 418 in the proximal end 420. In one embodiment, the deep trenches 424 are each about three times wider and three times deeper than the shallow trenches 422.

The shallow trenches 422 and the deep trenches 424 are configured to receive the terminal ends of the solid wires 102, and hold the terminal ends against the electrodes 112 when clamp structure 108 is attached to tube 110. An adhesive may be inserted into one or more of holes 406 and notches 404 and 418 to provide a more secure interconnection between the terminal ends of the solid wires 102 and the electrodes 112.

Figure 5:
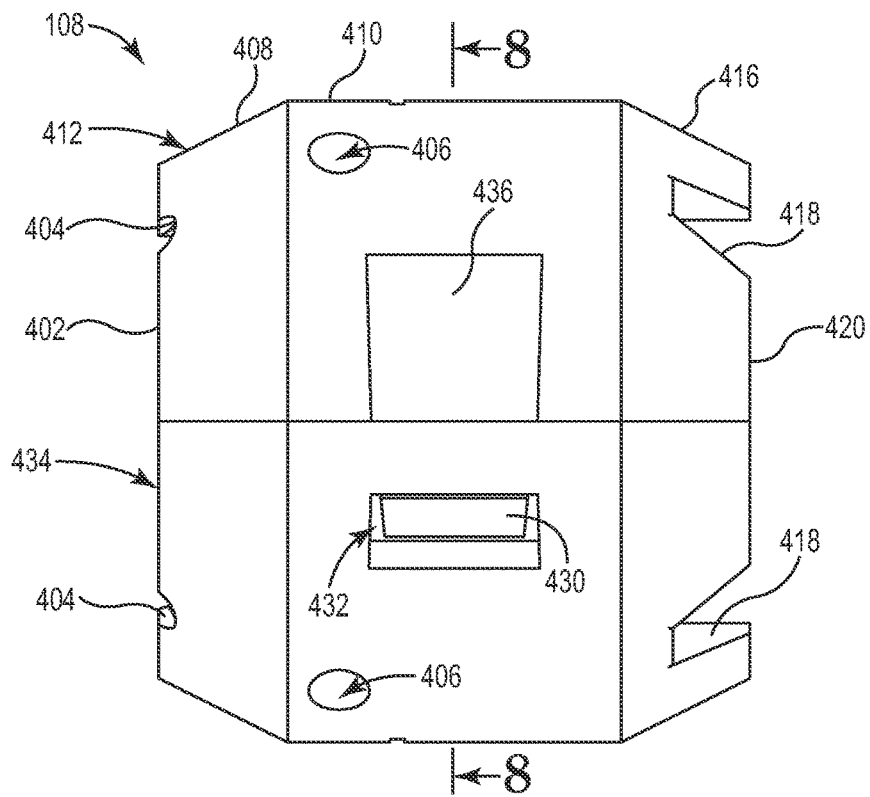
FIG. 5 is a diagram illustrating a side view of the interconnection structure shown in FIG. 4 according to one embodiment.

FIG. 5 is a diagram illustrating a side view of the interconnection structure 108 shown in FIG. 4 according to one embodiment. As shown in FIG. 5, the flexible clip 436 of the male element 412 includes a protrusion 430 that is inserted into the opening 432 in the female element 434. Another clip 436 is positioned on the opposite side of the clamp structure 108. The clips 436 hold the male element 412 and the female element 434 together. Clips 436 can be pushed inward to allow the male element 412 to be separated from the female element 434.

Figure 6:
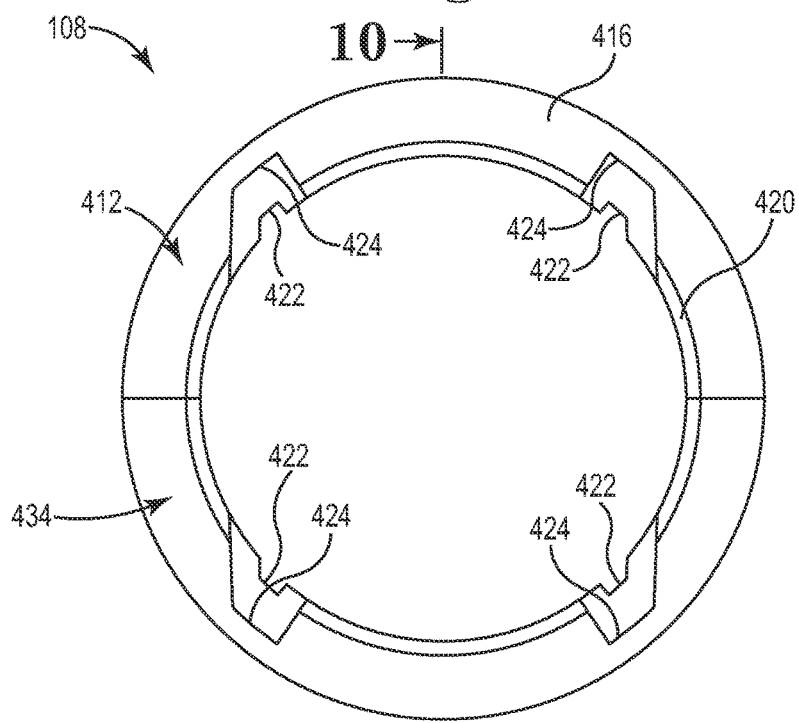
FIG. 6 is a diagram illustrating a bottom view of a proximal end of the interconnection structure shown in FIG. 4 according to one embodiment.

FIG. 6 is a diagram illustrating a bottom view of a proximal end 420 of the interconnection structure 108 shown in FIG. 4 according to one embodiment. As shown in FIG. 6, each one of the shallow trenches 422 is paired with and is longitudinally aligned with one of the deep trenches 424. The trenches 422 and 424 are substantially evenly spaced apart around a circumference of the interior surface 426.

Figure 7:
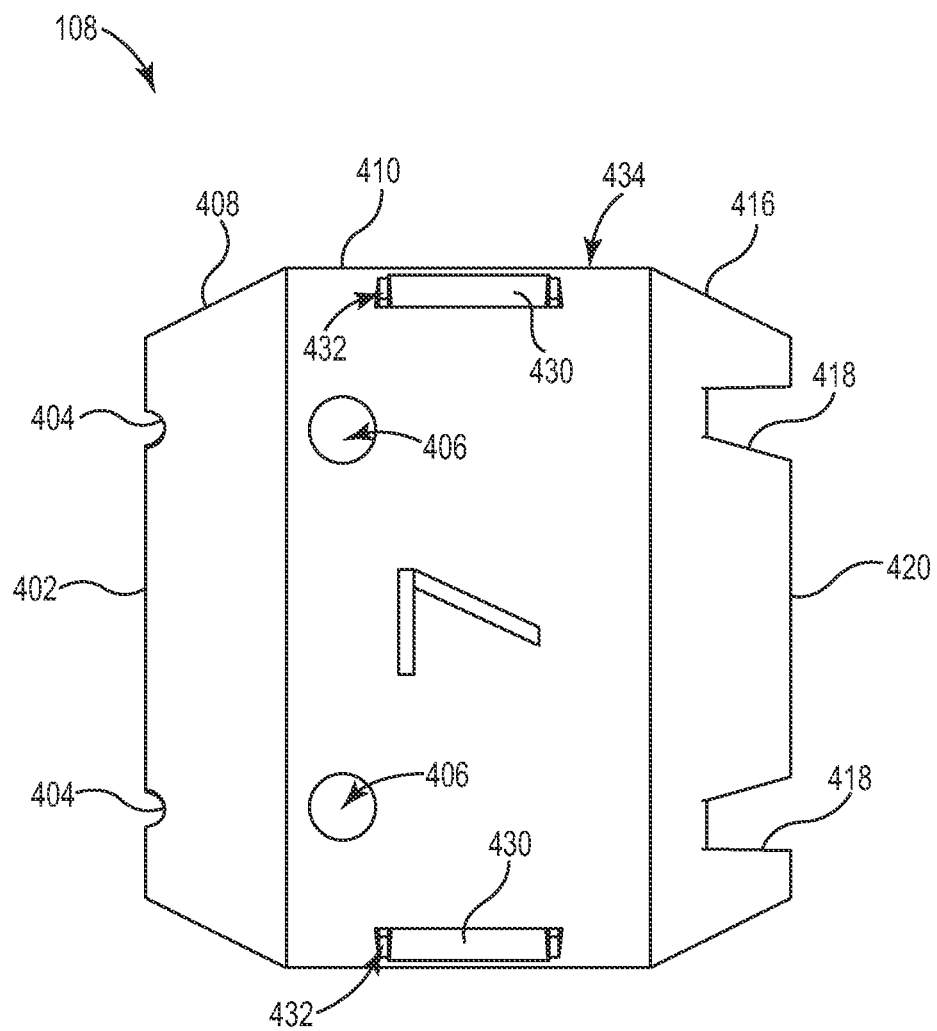
FIG. 7 is a diagram illustrating a side view of a female element of the interconnection structure shown in FIG. 4 according to one embodiment.

FIG. 7 is a diagram illustrating a side view of a female element 434 of the interconnection structure 108 shown in FIG. 4 according to one embodiment. As shown in FIG. 7, the protrusions 430 of the two flexible clips 436 of the male element 412 are inserted into respective openings 432 in the female element 434. The clips 436 hold the male element 412 and the female element 434 together, and can be pushed inward to allow the male element 412 to be separated from the female element 434.

Figure 8:
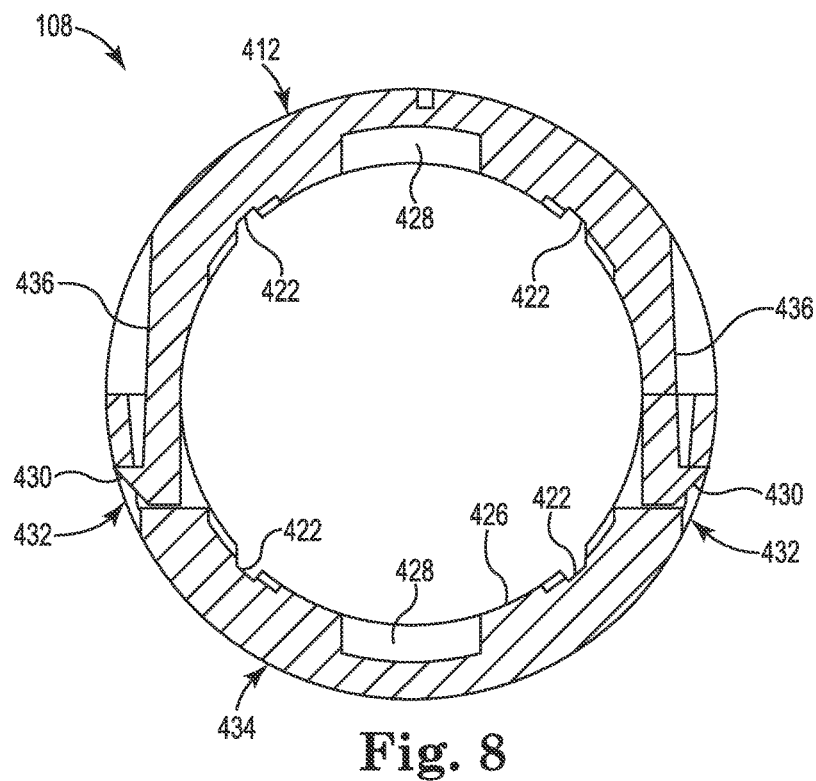
FIG. 8 is a diagram illustrating a cross-sectional view along section lines 8-8 in FIG. 5 according to one embodiment.

FIG. 8 is a diagram illustrating a cross-sectional view along section lines 8-8 in FIG. 5 according to one embodiment. As shown in FIG. 8, clamp structure 108 includes two cavities 428 positioned on opposing sides of the interior surface 426. The two clips 436 on the male element 412 extend down into the interior of the female element 434, and the protrusions 430 of the clips 436 extend outward and through the respective openings 432 in the female element 434. The trenches 422 are substantially evenly spaced apart around a circumference of the interior surface 426.

Figure 9:
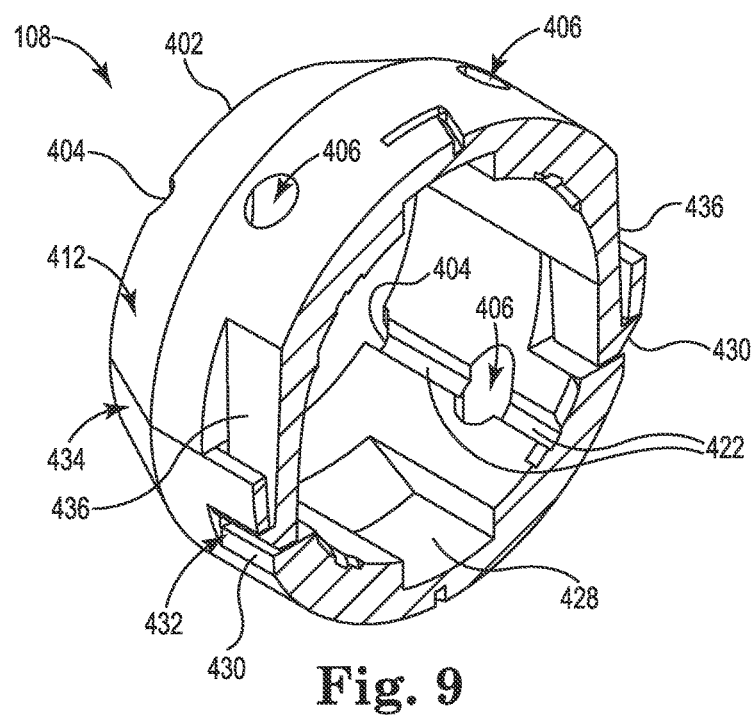
FIG. 9 is a diagram illustrating a perspective view of the cross-section of the interconnection structure shown in FIG. 8 according to one embodiment.

FIG. 9 is a diagram illustrating a perspective view of the cross-section of the interconnection structure 108 shown in FIG. 8 according to one embodiment. As shown in FIG. 9, the shallow trenches 422 longitudinally extend proximally and distally from a respective one of the holes 406. The shallow trenches 422 longitudinally extend from a distal end of a respective one of the deep trenches 424 to a respective one of the notches 404 in the distal end 402.

Figure 10:
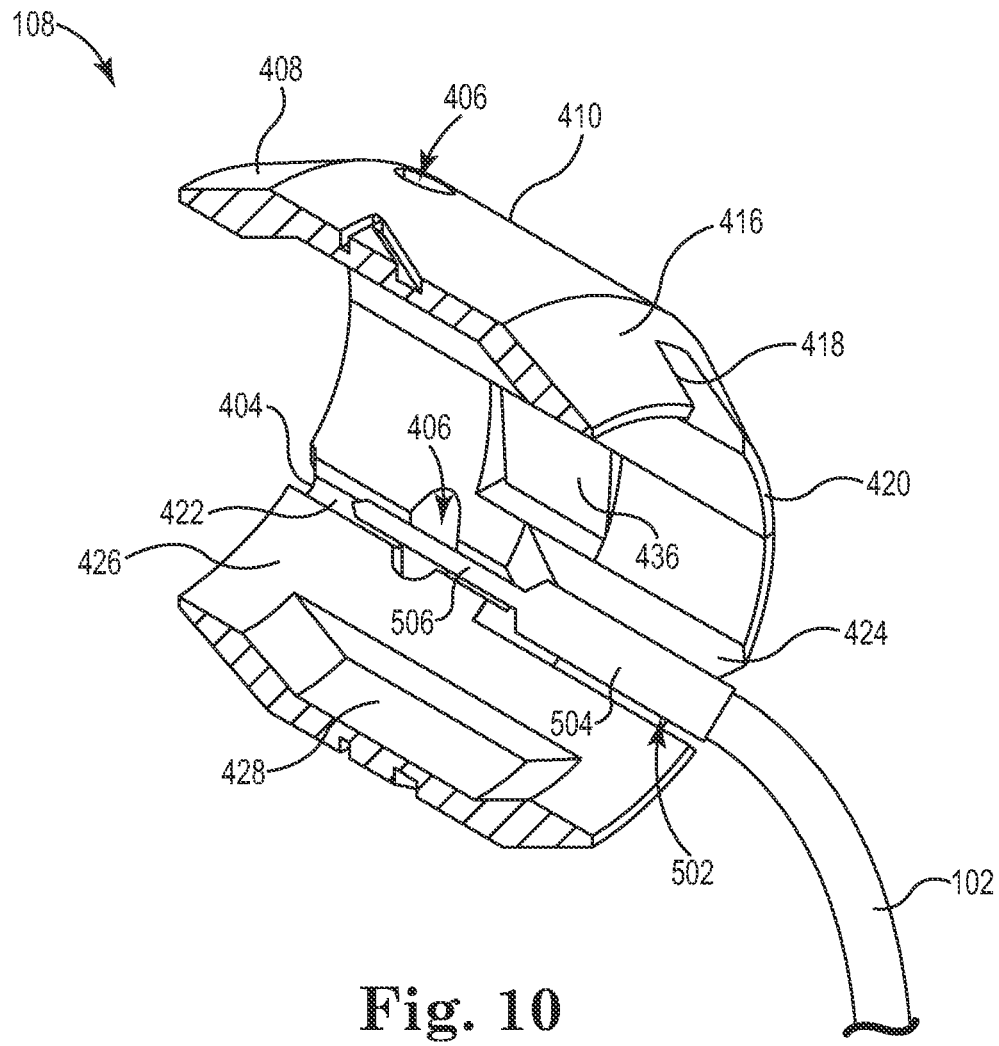
FIG. 10 is a diagram illustrating a cross-sectional perspective view along section lines 10-10 in FIG. 6 according to one embodiment.

FIG. 10 is a diagram illustrating a cross-sectional perspective view along section lines 10-10 in FIG. 6 according to one embodiment. As shown in FIG. 10, the terminal end 502 of one of the solid wires 102 has been placed within the clamp structure 108. The terminal end 502 of the solid wire 102 includes a wide proximal portion 504 and a narrow distal portion 506. The deep trench 424 is sized to receive the wide proximal portion 504 of the terminal end 502. The shallow trench 422 is sized to receive the narrow distal portion 506 of the terminal end 502. The narrow distal portion 506 of the terminal end extends across the hole 406 on the interior surface 426.

In the embodiment shown in FIG. 10, a total of four solid wires 102 can be placed into the clamp structure 108 at the four different sets of shallow trenches 422 and deep trenches 424. In one embodiment, male element 412 and female element 434 are initially separated from one another to allow the placement of the terminal ends of the solid wires 102 within the clamp structure 108. The male element 412 and female element 434 are then positioned on the tube 510 with each of the terminal ends of the solid wires 102 aligned with a respective one of the electrodes 112 on the tube 110. The male element 412 and the female element 434 are then clipped together on the tube 110. Once the male element 412 and the female element 434 have been clipped together on the tube 110, the clamp structure 108 securely holds each of the terminal ends of the solid wires 102 against a respective one of the electrodes 112 on the tube 110. An adhesive may be inserted into one or more of holes 406 and notches 404 and 418 to provide a more secure interconnection between the terminal ends of the solid wires 102 and the electrodes 112. In another embodiment, the male element 412 and the female element 434 are first clipped together on the tube 110, and then the terminal ends of the wires 102 are inserted through the notches 418 and into the trenches 422 and 424. The holes 406 allow a user to view the tube 110, and help the user to determine when the electrodes 112 are aligned with the holes 406.

Figure 11:
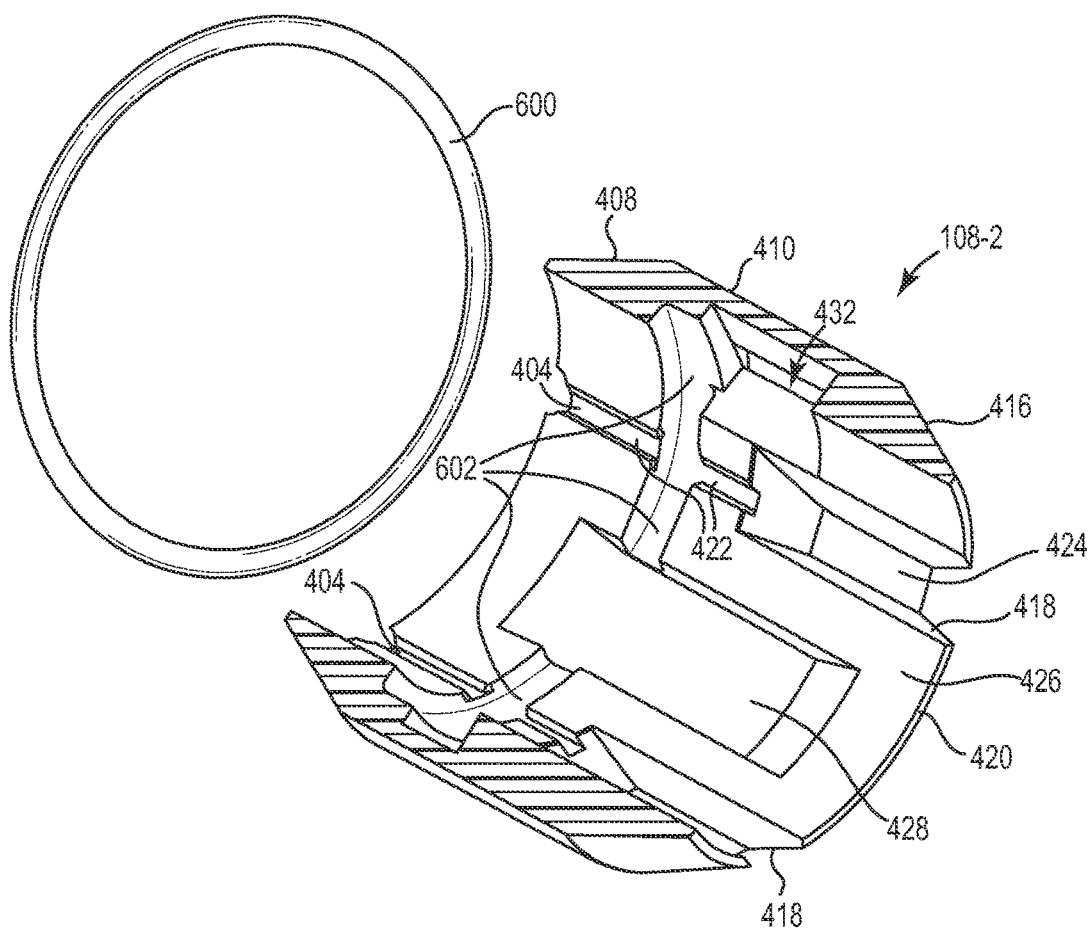
FIG. 11 is a diagram illustrating a perspective view of a portion of an interconnection structure according to another embodiment.

FIG. 11 is a diagram illustrating a perspective view of a portion of an interconnection structure 108-2 according to another embodiment. In the illustrated embodiment, interconnection structure 108-2 is configured in substantially the same manner as interconnection structure 108 (FIGS. 4-10), except that holes 406 have been removed and an O-ring cavity 602 has been added to structure 108-2. The O-ring cavity 602 is configured to receive a compliant O-ring 600. The O-ring cavity 602 is formed in the interior surface 426 of the structure 108-2, and extends laterally around the entire interior circumference of the cylindrical central portion 410. The O-ring cavity 602 runs perpendicular to the trenches 422 and 424, and intersects each of the shallow trenches 422.

In the illustrated embodiment, the fit between the structure 108-2 and the tube 110 will not be an interference fit. When interconnection structure 108-2 is attached to tube 110, the narrow distal portions 506 of the terminal ends 502 of the solid wires 102 (FIG. 10) are placed in trenches 422 on top of the O-ring 600, and the O-ring 600 pushes the terminal ends 502 against respective ones of the electrodes 112. The use of O-ring 600 facilitates an easier assembly and loosens tolerance requirements.

One embodiment is directed to a clamp for securing a terminal end of a wire to a surface electrode formed on a cylindrical tube. The clamp includes a first semicylindrical element, and a second semicylindrical element configured to be attached to the first semicylindrical element to form a tubular clamp structure that is adapted to be clamped around the cylindrical tube. The tubular clamp structure includes an interior surface configured to securely hold a terminal end of a wire against a surface electrode formed on the cylindrical tube.

The tubular clamp structure according to one embodiment includes a cylindrical central portion positioned between a tapered distal end portion and a tapered proximal end portion. The tapered distal end portion and the tapered proximal end portion are configured to form a friction fit against the cylindrical tube. A plurality of notches is formed in a distal end of the tapered distal end portion, and each of the notches is configured to be aligned with a surface electrode on the cylindrical tube. A plurality of notches is formed in a proximal end of the tapered proximal end portion, and each of the notches is configured to be aligned with a surface electrode on the cylindrical tube. A plurality of holes is formed in the cylindrical central portion, and each of the holes is configured to be aligned with a surface electrode on the cylindrical tube.

In one embodiment, the interior surface of the tubular clamp structure includes a plurality of trench elements formed therein, and each of the trench elements is configured to receive a terminal end of a wire and secure the terminal end of the wire to a surface electrode formed on the cylindrical tube. Each of the trench elements according to one embodiment includes a shallow trench longitudinally aligned with a deep trench, wherein the deep trench is deeper and wider than the shallow trench.

In one embodiment, the first semicylindrical element is a female element, and the second semicylindrical element is a male element with a clip extending therefrom that is configured to be inserted into the female element to attach the male element and the female element together. The interior surface of the tubular clamp structure according to one embodiment is configured to securely hold a terminal end of a wire against a surface electrode formed on an exterior surface of an endotracheal tube. The interior surface of the tubular clamp structure according to one embodiment includes an O-ring cavity formed therein that is configured to receive a compliant O-ring that pushes a terminal end of a wire against a surface electrode formed on the cylindrical tube.

Another embodiment is directed to a cylindrical apparatus, which includes a cylindrical tube having an exterior surface. Electrodes are formed on the exterior surface of the cylindrical tube. A tubular clamp structure is configured to be clamped around the cylindrical tube. The tubular clamp structure includes an interior surface configured to securely hold terminal ends of wires to respective ones of the electrodes formed on the cylindrical tube.

In one embodiment, the tubular clamp structure includes a cylindrical central portion positioned between a tapered distal end portion and a tapered proximal end portion. A plurality of notches is formed in a distal end of the tapered distal end portion, and each of the notches is configured to be aligned with one of the electrodes on the cylindrical tube. A plurality of notches is formed in a proximal end of the tapered proximal end portion, and each of the notches is configured to be aligned with one of the electrodes on the cylindrical tube. A plurality of holes is formed in the cylindrical central portion, and each of the holes is configured to be aligned with one of the electrodes on the cylindrical tube.

In one embodiment, the interior surface of the tubular clamp structure includes a plurality of trench elements formed therein, and each of the trench elements is configured to receive a terminal end of a wire and secure the terminal end of the wire to one of the electrodes formed on the cylindrical tube. Each of the trench elements according to one embodiment includes a shallow trench longitudinally aligned with a deep trench, wherein the deep trench is deeper and wider than the shallow trench. In one embodiment, the tubular clamp structure includes a semicylindrical female element and a semicylindrical male element with a clip extending therefrom that is configured to be inserted into the female element to attach the male element and the female element together.

Yet another embodiment is directed to an apparatus for monitoring EMG signals of a patient's laryngeal muscles. The apparatus includes an endotracheal tube having an exterior surface. Conductive electrodes are formed on the exterior surface of the endotracheal tube. The conductive electrodes are configured to receive the EMG signals from the laryngeal muscles when the endotracheal tube is placed in a trachea of the patient. Conductors are respectively coupled to the conductive electrodes and configured to carry the EMG signals received by the conductive electrodes to a processing apparatus. A tubular clamp is configured to be clamped around the endotracheal tube and hold terminal ends of the conductors in contact with the conductive electrodes.

Although embodiments have been described in the context of an EMG endotracheal tube, it will be understood that the techniques disclosed herein are applicable to connecting wires to surface electrodes formed on any cylindrical object or non-planar surface. One embodiment provides a low cost and reliable method for connecting wires to electrodes formed (e.g., printed) on a cylindrical surface, without the use of flex circuits, conductive epoxies, and soldering.

Although the present disclosure has been described with reference to preferred embodiments, workers skilled in the art will recognize that changes can be made in form and detail without departing from the spirit and scope of the present disclosure.

What is claimed is:

1. An apparatus, comprising:
   a cylindrical tube having an exterior surface;
   a surface electrode formed on the exterior surface of the cylindrical tube;
   a wire having a terminal end;
   a first semicylindrical element;
   a second semicylindrical element configured to be attached to the first semicylindrical element to form a tubular clamp structure that is adapted to be clamped around the cylindrical tube and secure the terminal end of the wire to the surface electrode; and
   wherein the tubular clamp structure includes an interior surface with a trench element formed therein, wherein the trench element includes a longitudinal shallow trench longitudinally aligned with a longitudinal deep trench and longitudinally extending from a distal end of the longitudinal deep trench, wherein the longitudinal deep trench is deeper than the longitudinal shallow trench and laterally wider than the longitudinal shallow trench, and wherein the trench element is sized to receive and securely hold the terminal end of the wire directly against the surface electrode formed on the exterior surface of the cylindrical tube.

2. The apparatus of claim 1, wherein the tubular clamp structure includes a cylindrical central portion positioned between a tapered distal end portion and a tapered proximal end portion.

3. The apparatus of claim 2, wherein the tapered distal end portion and the tapered proximal end portion are configured to form a friction fit against the cylindrical tube.

4. The apparatus of claim 2, and further comprising:
   a plurality of notches formed in a distal end of the tapered distal end portion, wherein each of the notches is configured to be aligned with a respective one of a plurality of surface electrodes on the cylindrical tube.

5. The apparatus of claim 2, and further comprising:
   a plurality of notches formed in a proximal end of the tapered proximal end portion, wherein each of the notches is configured to be aligned with a respective one of a plurality of surface electrodes on the cylindrical tube.

6. The apparatus of claim 2, and further comprising:
   a plurality of holes formed in the cylindrical central portion, wherein each of the holes is configured to be aligned with a respective one of a plurality of surface electrodes on the cylindrical tube.

7. The apparatus of claim 1, wherein the interior surface includes a plurality of trench elements formed therein, and wherein each of the trench elements is configured to receive a respective one of a plurality of terminal ends of wires and secure the respective terminal end to a respective one of a plurality of surface electrodes formed on the cylindrical tube.

8. The apparatus of claim 7, wherein each of the trench elements includes a shallow trench longitudinally aligned with a deep trench.

9. The apparatus of claim 8, wherein the deep trench of each of the trench elements is deeper and wider than the shallow trench of each of the trench elements.

10. The apparatus of claim 1, wherein the first semicylindrical element is a female element, and wherein the second semicylindrical element is a male element with a clip extending therefrom that is configured to be inserted into the female element to attach the male element and the female element together.

11. The apparatus of claim 1, wherein the interior surface includes an O-ring cavity formed therein that is configured to receive a compliant O-ring that pushes the terminal end of the wire against the surface electrode formed on the cylindrical tube.

12. A cylindrical apparatus, comprising:
    a cylindrical tube having an exterior surface;
    electrodes formed on the exterior surface of the cylindrical tube;
    wires; and
    a tubular clamp structure clamped around the cylindrical tube, wherein the tubular clamp structure includes an interior surface securely holding terminal ends of the wires directly to respective ones of the electrodes formed on the exterior surface of the cylindrical tube.

13. The cylindrical apparatus of claim 12, wherein the tubular clamp structure includes a cylindrical central portion positioned between a tapered distal end portion and a tapered proximal end portion.

14. The cylindrical apparatus of claim 13, and further comprising:
    a plurality of notches formed in a distal end of the tapered distal end portion, wherein each of the notches is aligned with one of the electrodes on the cylindrical tube.

15. The cylindrical apparatus of claim 13, and further comprising:
    a plurality of notches formed in a proximal end of the tapered proximal end portion, wherein each of the notches is aligned with one of the electrodes on the cylindrical tube.

16. The cylindrical apparatus of claim 13, and further comprising:

a plurality of holes formed in the cylindrical central portion, wherein each of the holes is aligned with one of the electrodes on the cylindrical tube.

17. The cylindrical apparatus of claim 12, wherein the interior surface includes a plurality of trench elements formed therein, and wherein each of the trench elements is configured to receive a respective one of the terminal ends of wires and secure the respective terminal end to one of the electrodes formed on the cylindrical tube.

18. The cylindrical apparatus of claim 17, wherein each of the trench elements includes a shallow trench longitudinally aligned with a deep trench, and wherein the deep trench is deeper and wider than the shallow trench.

19. An apparatus for monitoring EMG signals of a patient's laryngeal muscles, comprising:
   an endotracheal tube having an exterior surface;
   conductive electrodes formed on the exterior surface of the endotracheal tube, the conductive electrodes configured to receive the EMG signals from the laryngeal muscles when the endotracheal tube is placed in a trachea of the patient;
   conductors respectively coupled to the conductive electrodes to carry the EMG signals received by the conductive electrodes to a processing apparatus; and
   a tubular clamp clamped around the endotracheal tube and holding terminal ends of the conductors in direct contact with the conductive electrodes formed on the exterior surface of the endotracheal tube.

* * * * *